United States Patent
Daum et al.

[11] Patent Number: 6,120,517
[45] Date of Patent: Sep. 19, 2000

[54] CONTROLLED-ARTIFACT MAGNETIC RESONANCE INSTRUMENTS

[75] Inventors: Wolfgang Daum, Schwerin; Axel Winkel, Zapel Hoff, both of Germany

[73] Assignee: Daum GmbH, Schwerin, Germany

[21] Appl. No.: 09/135,194

[22] Filed: Aug. 17, 1998

Related U.S. Application Data

[63] Continuation-in-part of application No. 08/639,215, Apr. 26, 1996, Pat. No. 5,895,401.

[51] Int. Cl.⁷ ..................................................... A61B 17/32
[52] U.S. Cl. .............................................................. 606/167
[58] Field of Search .................... 606/167, 170, 606/185, 222; 128/898, 899

[56] References Cited

U.S. PATENT DOCUMENTS

| | | | |
|---|---|---|---|
| 4,662,891 | 5/1987 | Noiles | 606/80 |
| 4,765,335 | 8/1988 | Schmidt et al. | 606/158 |
| 4,849,208 | 7/1989 | Stavrianopoulos | 424/1.53 |
| 5,135,608 | 8/1992 | Okutani | 156/643 |
| 5,167,725 | 12/1992 | Clark et al. | 428/680 |
| 5,298,112 | 3/1994 | Hayasaka et al. | 156/643 |
| 5,549,612 | 8/1996 | Yapp et al. | 606/73 X |

OTHER PUBLICATIONS

Copy of Product Literature "Biopsy Needle" publicly available Nov. 1995.
Copy of Product Literature "Conversion Table" publicly available Nov. 1995.

*Primary Examiner*—Michael Buiz
*Assistant Examiner*—Vikki H. B. Trinh
*Attorney, Agent, or Firm*—Altera Law Group LLC

[57] ABSTRACT

The present invention provides materials and methods for preparing medical instruments which cause reduced or enhanced artifact on diagnostic images. According to the invention, a reduced artifact instrument may be prepared using titanium alloy compositions or plastic compositions disclosed herein. An enhanced artifact instrument may be prepared by incorporating artifact causing materials into artifact free instruments. Such instruments are suitable for use during diagnostic imaging procedures, for example, magnetic resonance imaging. The invention also provides compositions and methods for removing magnetic contaminants from the surface of a medical instrument or an alloy material.

20 Claims, 14 Drawing Sheets

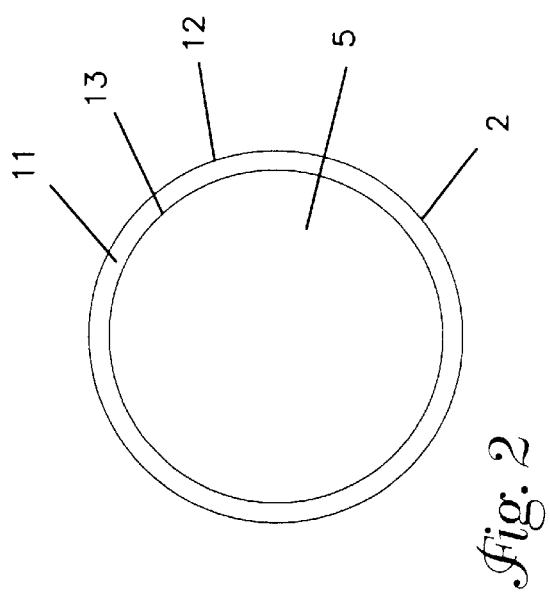
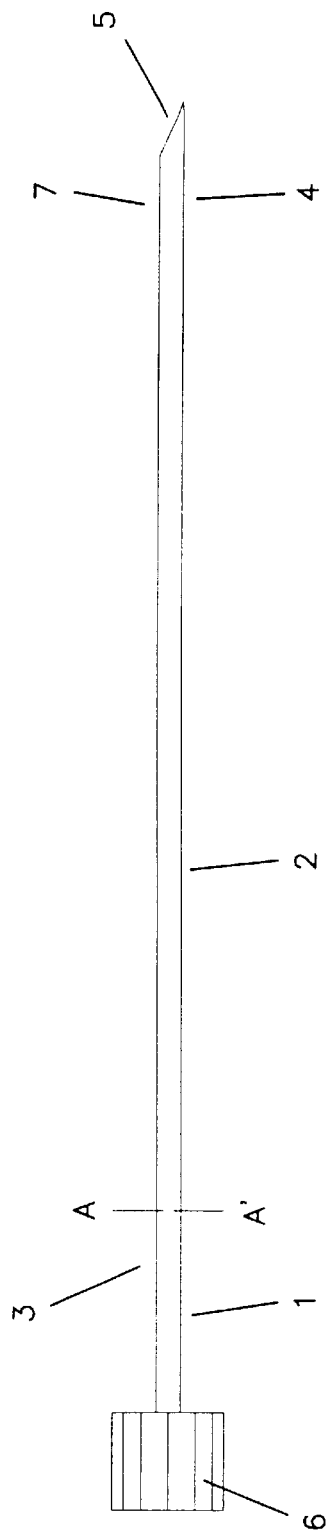
Fig. 2
Fig. 1

CONTROLLED-ARTIFACT MAGNETIC RESONANCE INSTRUMENTS

CROSS-REFERENCE TO RELATED APPLICATIONS

The present application is a continuation-in-part of U.S. Ser. No. 08/639,215, filed Apr. 26, 1996, now U.S. Pat. No. 5,895,401, the entire disclosure of which is incorporated herein by reference.

FIELD OF THE INVENTION

The present invention is directed to controlling the artifact caused by medical and surgical instruments on diagnostic images. The invention provides for both increasing and decreasing the artifact created by an instrument on a diagnostic image. The invention is also directed towards new penetrating instruments configured for less chance of structural deformity during use. Medical and surgical instruments of the invention are particularly suited for use during diagnostic imaging procedures, for example, magnetic resonance imaging (MRI).

BACKGROUND OF THE INVENTION

Medical imaging technology has advanced rapidly in recent years. A major thrust of the advancement has come through the use of nuclear magnetic resonance (NMR) technology to provide clinical magnetic resonance imaging (MRI) systems.

The principles of NMR were first described in about 1946, however, MRI instrumentation has only been used since 1973. In the time period since 1973, MRI has rapidly established itself as a superior imaging modality, in certain situations, relative to x-ray, CT scanning and ultrasound. For example, MRI is a modality of choice for high resolution imaging of soft tissue. In addition, use of proper MRI technique allows distinction of areas of edema, hemorrhage, tumors (e.g. bone tumor) and flowing blood which are typically difficult to distinguish using, for example, x-ray CT.

Many MRI's which are presently available create a magnetic field using cylindrical superconducting magnets which may obstruct access to the patient during scanning. More recently, open MRI systems have become available which permit access to the patient during imaging procedures. Hence, this allows the practitioner an opportunity to perform diagnostic or therapeutic procedures while performing MRI scans. This new field in medicine is called MRT (magnetic resonance therapy). Unfortunately, however, many of the instruments which may be used to perform procedures during imaging create artifact on the resulting image.

Accordingly, there is a need for materials that can be used during diagnostic imaging procedures, especially MRI, with controlled production of artifact on the resulting image. There is also a need for instruments which may be used during scanning with reduced obstruction of visualization during scanning. Moreover, there is a need for instruments which minimally obscure visualization during scanning and which can resist structural deformity during use. Furthermore, there is the need to develop a technology to control the artifact of the instrument which is caused by the magnetic property of its material.

SUMMARY OF THE INVENTION

The invention teaches medical instruments for control of artifact caused by instruments which may appear when the instrument is present in the viewing field of a diagnostic image. Materials suitable for instruments according to the invention include titanium alloy compositions, plastics, ceramics, glass fiber enhanced plastics and ferromagnetic materials.

In one embodiment, the invention provides low artifact medical instruments composed of a titanium alloy containing 2.5%–7% aluminum; 2%–5% vanadium; and titanium to 100% total. The medical instrument may further include up to 0.3% iron. In one preferred embodiment, a medical instrument may include titanium as ISO 3.7034 or 3.7035.

According to the invention, medical instruments which cause artifact, are low artifact or artifact free may also be prepared from glass fiber enhanced plastic.

In another embodiment, the invention provides a method for removing magnetic contaminants from the surface of an alloy composition, for example, an alloy containing medical instrument. The advantage of a low artifact medical instrument, containing an alloy material, may be lost due to tooling of the medical instrument with ferromagnetic containing tools. However, the invention provides for reduction of magnetic contaminants by wet chemical etching of the surface of the alloy instrument. According to the method, a wet chemical etching composition is prepared by combining an acid, HX, wherein X is a halogen, and nitric acid. The contaminated alloy is then contacted with the wet chemical etching composition as described herein.

The invention also provides for enhancing the artifact which is created on a diagnostic image by a medical instrument. According to this embodiment, a medical instrument can include at least one lumen which includes a removable artifact material. In a preferred embodiment, a medical instrument according to this aspect of the invention is a catheter.

In a preferred embodiment, a catheter which causes an enhanced artifact on MRI images is described. According to this embodiment, a catheter includes at least two lumens one of which is closed at the distal end. An artifact material which is suitable for the production of a positive or negative contrast is inserted within the lumen having a closed distal end. Suitable artifact materials include positive and negative contrast agents, for example, a ferromagnetic fiber.

Alternatively, an artifact producing medical instrument may be prepared by depositing a thin layer of artifact material onto an artifact free medical instrument. Various methods for depositing an artifact material onto an artifact free material are known in the art and disclosed herein.

The invention further provides an instrument which includes both artifact and artifact free materials. In a preferred embodiment such an instrument includes, for example, a "tumor localizer". According to this embodiment, a tumor localizer includes a rigid outer tube, an artifact free tube which is removably inserted within the rigid outer tube, and a localizer wire prepared from an artifact material which is removably inserted within the artifact free tube.

A low artifact or artifact free instrument of the invention is generally capable of resisting loss of structural configuration when penetrating or cutting a physiological tissue. The invention, however, also provides an improved penetrating end having enhanced resistance to distortion or bending upon penetration of a tissue.

It will be noted that in several places throughout the specification, guidance is provided through lists of examples. In each instance, the recited lists serve only as a representative group. It is not meant, however, that the lists are exclusive.

BRIEF DESCRIPTION OF THE DRAWINGS

FIG. 1 is a side elevational view of an embodiment of a penetrating instrument according to the invention.

FIG. 2 is a cross sectional view of the penetrating instrument shown in FIG. 1 taken at A–A'.

DETAILED DESCRIPTION OF THE INVENTION

Figure 3:
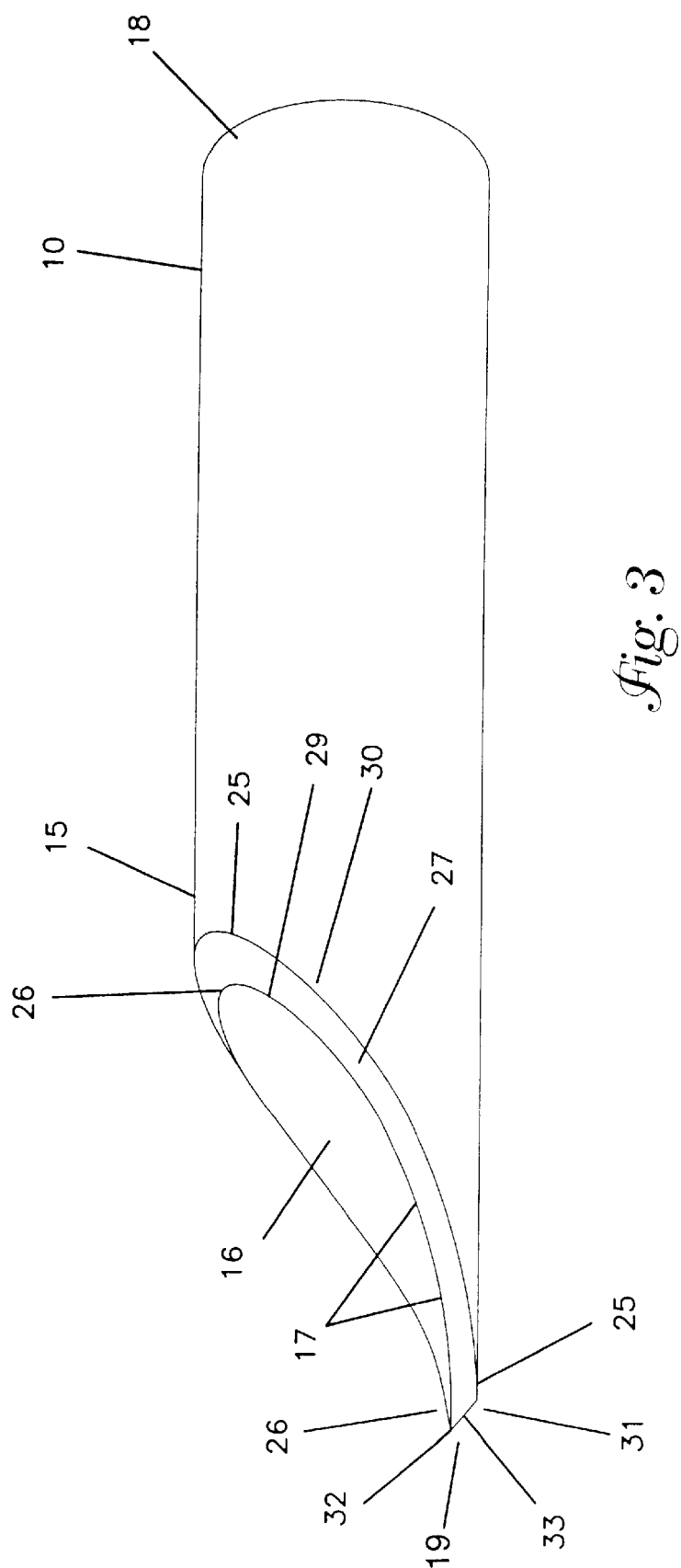
FIG. 3 is a perspective view of an embodiment of a penetrating end of a penetrating instrument of the invention.

The present invention is directed towards control of artifact caused by medical and surgical instruments used during diagnostic imaging. In one embodiment, the invention provides medical and surgical instruments composed of alloy compositions which cause low artifact on diagnostic images. In another embodiment, the invention provides for enhancement of the artifact caused by medical and surgical instruments on diagnostic images. According to the invention, "control" of image artifact means increasing or decreasing the image artifact depending on the needs of the operator. An instrument of the invention is suited for use during diagnostic imaging procedures and is particularly suited for use during, for example, magnetic resonance imaging (MRI) scanning.

The invention also provides an improved penetrating tip arrangement for a penetrating instrument having an enhanced ability to withstand structural deformation during penetration. This is particularly advantageous when instruments, such as needles, are prepared from "soft" materials which may have a tendency to deform when used to penetrate certain tissues.

I. LOW ARTIFACT COMPOSITION FOR MEDICAL AND SURGICAL INSTRUMENTS

As used herein, "artifact" means an artificial or distorted image present on a diagnostic image which is caused by an instrument, procedure or other form of intervention occurring during the imaging procedure. The artifact created on a diagnostic image by a given procedure or material varies. According to the invention, an "artifact material" is any material which shows a distinct artifact in an image, for example, steel or ferromagnetic materials. Such artifacts may distort or obstruct the interpretation of the diagnostic image. However, such artifact materials may also provide for easy detection of an artifact causing device. Instruments prepared from an artifact material which have a dimension "X" typically will cause an artifact on the image which is often greater than 3X.

According to the invention a "low artifact" material may cause an artifact on the image which is not significant enough to prevent accurate interpretation of the image. Such materials which causes a "low" artifact are described in Section I of the present specification.

An "artifact free" material is a material which creates a minimal artifact on a diagnostic image, for example, certain types of plastic. These materials typically comprise a magnetic susceptibility which is the size of water (or free protons).

In one embodiment, the present invention provides alloy materials which produce "low artifact" when used during diagnostic imaging procedures. In one embodiment of the invention, an alloy composition of the invention is useful for the preparation of medical instruments used during performance of diagnostic imaging procedures. As used herein, a "medical" instrument refers to any instrument which may be used during performance of a medical or surgical diagnostic or therapeutic procedure. Such instruments include, for example, biopsy needles, injection needles, catheters, forceps, stethoscopes and similar instruments.

One advantage of a medical instrument prepared with a composition of the invention is that the presence of the instrument in the field of the imaging system, for example MRI, may cause less distortion of the structure imaged thus enhancing the accuracy of interpretation of the image. Moreover, while the instruments of the invention are particularly suited for use during open MRI imaging, the inventor recognizes that instruments of the invention may also be used in or near the imaging field of non-open (conventional) MRI or other diagnostic imaging modalities.

As used herein, "open MRI" refers to MRI imaging systems whose magnetic field producing magnets are arranged in such a manner as to allow access to the patient during MRI scanning.

A composition used to prepare an instrument according to the invention is, preferably, a titanium alloy. Titanium (Ti) is a particularly useful component of the alloy because it produces low artifact defects in an image created by MRI. Titanium of grade 1–5 of the American Society for Testing and Materials (ASTM) standard can be used to cause only low artifact defects in the image. However, typically, titanium of this grade is too soft for use in instruments which may be used to cut or penetrate a physiological tissue such as skin, muscle, fascia, blood vessels, parenchymal organs, etc.

As used herein "soft" refers to a material composition which has a greater tendency to lose its structural configuration when used to cut or penetrate a physiological tissue. Such loss of structural configuration include, for example, bending of the tip of a needle, blunting of the tip of a needle or bending or blunting of the sharp edge of an instrument. In one embodiment, the present invention overcomes the problem of soft materials, such as titanium, by preferably using a titanium alloy. The titanium component of a titanium alloy suitable for the invention may be present in a weight percentage of at least 80%, preferably, greater than 85%.

In a preferred embodiment, the titanium alloy may also include the element aluminum (Al). Aluminum suitable for a composition of the invention includes any aluminum which when combined to form a titanium alloy of the invention does not nullify the low artifact characteristics of the alloy. Aluminum may be present in the titanium alloy in a weight percentage of 1–10%, preferably about 2.5–7%.

A titanium alloy of the invention may also include a compound to provide increased "hardness" to the alloy. As used herein when referring to an alloy of the invention, the term "hard" and derivations thereof refers to a characteristic of a material which provides resistance to deformation when an instrument prepared from a composition of the invention is used to cut or penetrate a physiological tissue. Preferably, a component of the alloy which increases hardness is harder than titanium. One such preferred compound is vanadium (V). The vanadium component of a titanium alloy of the invention may be present in a range of 1% to 5%, preferably 1.5% to 4%.

A titanium alloy of the invention may also include small amounts of iron (Fe).

While it is understood that other metallic materials may be added to a composition of the invention, the components disclosed herein provide a preferred alloy composition for producing medical instruments. In a typical embodiment, a medical instrument of the invention may be prepared from a titanium alloy which complies with (ASTM) grade 9 or Ti-3Al-2.5V (ISO) 3.7194 (or 3.7195). The percentage of the components of the alloy according to this embodiment of the invention are: Ti 94.5%; Al 3.0%; and V 2.5%.

Another suitable titanium alloy, useful according to the invention, complies with ASTM grade 5 or ISO 3.765 or 3.7165. The percentage of the alloy components according to this embodiment of the invention are: Ti 90%; Al 6%; and V 4%. These titanium alloys are available from UTI-Uniform Tubes, Inc. Collegeville, Pa. 19426-0992 or Fastener Technology Corporation, 7415 Fulton Avenue, North Hollywood, Calif. 91605 or Alphatec Manufacturing Inc., 42-160 State Street, Palm Desert, Calif. 92211.

In another embodiment, a titanium alloy suitable for instruments according to the invention includes: Ti greater than 95%; Al 2.5%–3.3%; and V 2.0%–2.5%. An example of a particularly preferred titanium alloy composition containing greater than 95% titanium is:
Ti-3Al-2.5V. A particularly preferred embodiment includes titanium as ISO 3.7034 or 3.7035.

In still another embodiment of the invention, a titanium alloy of the invention may also include small amounts of iron (Fe). Two such iron containing compositions are Al 5.5%–6.75%, V 3.5%–4.5%, Fe up to 0.3%, Ti to 100% total; and Al 2.5%–3.5%, V 2.0%–3.0%, Fe up to 0.25%, Ti to 100% total.

A titanium alloy for an instrument of the invention may be used during a medical or surgical diagnostic or therapeutic procedure. The instruments are particularly advantageous for use during diagnostic imaging procedures, for example, MRI scanning. Medical instruments according to the invention, include, for example, biopsy needles, epidural needles, injection needles, scalpel blades, trocars, forceps, stethoscopes, knives, etc. A medical instrument may be prepared from a titanium alloy composition of the invention using methods known in the art. Such methods include, for example, milling, drilling and grinding.

According to the invention, when used to prepare injection needles or biopsy needles, a material of the invention can be used for preparing needles having an outside diameter of up to 18 mm or greater. Preferably, needles and biopsy needles of the invention are 0.3 mm (0.062 inch) –11.5 mm (0.445 inch) in diameter. Injection, epidural and biopsy needles of the invention are typically about 24 mm to 500 mm in length, preferably about 50 mm–200 mm. Trocars of the invention may have outside diameters of preferably up to 30 mm in diameter. Preferably, trocars of the invention are about 5 mm to 10 mm in diameter. Typical trocar lengths are about 50 mm to 250 mm in length, preferably about 100 mm to 150 mm.

In preparing an instrument of the invention, using some methods known in the art, it is not atypical to use tooling instruments which contain magnetic substances and being magnetic themselves. As a result, a titanium alloy of the invention may contain abrasives on its surface which will produce a higher image artifact after tooling compared to an instrument before tooling. It is believed that the higher post tooling image artifact is due to magnetic surface contamination of the tooled instrument by remnants of a ferrous based tool used to prepare the instrument.

Accordingly, another aspect of the present invention provides a method of wet chemical etching to reduce the surface magnetism of alloy instruments contaminated with magnetic substances. Although the inventor does not wish to be limited to a single theory, it is believed that wet chemical etching removes ferrous contaminants from the instrument.

A wet chemical etching composition may be prepared by combining an acid, HX, wherein "X" is a halogen and nitric acid. Halogens include Cl, F, Br and I. One example of a wet chemical etching composition according to the invention is prepared by combining 12 ml of 40% hydrofluoric acid (HF) 20 ml of 65% nitric acid ($HNO_3$) and 1800 ml $H_2O$. The etching is performed by dipping a machined instrument into the wet chemical etching composition (solution) for a short time e.g. 10–120 sec. The rate at which the etching occurs can be reduced by dilution with water.

Another example of a wet chemical etching composition is prepared by combining a 1:1 ratio of 25% $HNO_3$ and 25% HCl. According to this example, the etching is performed by dipping a machined instrument into the wet chemical etching composition for about 10–120 sec., typically about 90 sec. In one embodiment, hydrochloric acid (HCl) has been used without the nitric acid component. According to one example of this embodiment, a machined instrument can be dipped in 32% HCl.

The acidity of some wet chemical etching compositions can cause roughening of the surface of a device comprising titanium or a titanium alloy. Generally, the amount of surface roughening caused by any particular acid concentration of the etching composition increases with increased etching time. A roughened surface of the device can cause increased resistance when the instrument is passed along or against another surface. For example, if the device is a medical instrument such as a needle, a roughened exterior surface can increase resistance to passing the needle into a tissue.

Therefore, another aspect of the invention provides for application of a lubricant to the surface of a device that has been chemically etched according to the invention to reduce resistant forces when the device is passed along or against another surface, for example, passing into a tissue. A preferred lubricant is physiologically inert. As used herein, "physiologically inert" means that the lubricant will not cause a serious reaction in a tissue that is contacted by the lubricant.

A suitable surface lubricant can include such components as silicon, paraffin oil, etc. Suitable concentrations of the silicon in a lubricant solution are 1–60%, typically less than 50%, and preferably about 5–20%. A suitable commercially available silicon lubricant is MED-4159 available from Nusil Technology, 1040 Cindy Lane Carpinteria, Calif. 93013. MED-4159 contains silicon at a concentration of about 25–50%. Diluting MED-4159 with, for example, an alkane, such as hexane, to about 6–12% silicon is preferred. Other suitable lubricants include, for example, MED-6600 and MED-6605 also available from Nusil Company.

In use, the surface lubricant can be applied to the surface of a device by dipping, spraying, etc.

II. ENHANCING ARTIFACT CAUSED BY ARTIFACT FREE MEDICAL INSTRUMENTS

Medical instruments prepared from plastic or ceramic can be used in MRI. In some situations, however, a disadvantage of use of such materials is that they are essentially "artifact free" and produce no artifact on a diagnostic image when such artifact may be desirable. Hence, these instruments may not appear directly in the image. Rather, they will only be viewed by detection of geometrical displacement of the tissue which is caused by the instrument during a procedure. The guidance of such an instrument, for example, a catheter, under MRI may be very difficult.

Accordingly, another embodiment of the present invention provides for enhancing the artifact and hence, the visibility of an instrument used during an imaging procedure. While the herein described principle and method for enhancing image artifact may be used on many instruments, it will be exemplified by application to a catheter system.

According to this embodiment, a catheter is a flexible tube having one or more lumens for passing a medical instrument or a flowable material. In a preferred embodiment, the catheter includes at least two lumens. One of the two lumens is configured and arranged to contain an artifact material to create an artifact on a diagnostic image. Such artifact materials may create a negative or positive contrast artifact on a diagnostic image. Artifact materials suitable for the invention include, for example, lanthanides such as gadolinium and ferromagnetic compounds.

In one embodiment, at least two lumens are provided, wherein at least one lumen is closed at its distal end. According to this embodiment, the distally closed lumen is filled with a flowable liquid material which contains an artifact producing contrast agent. Such liquids may, for example, contain substances such as gadolinium or an other substance out of the lanthanides.

Figure 10A:
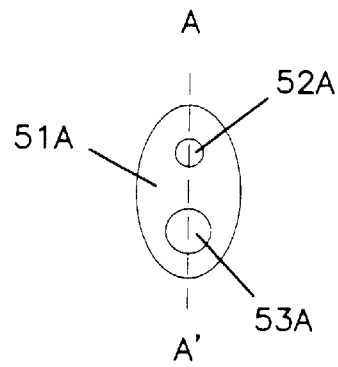
FIGS. 10a–d are cross-sectional views of catheters according to the invention.
Figure 10B:
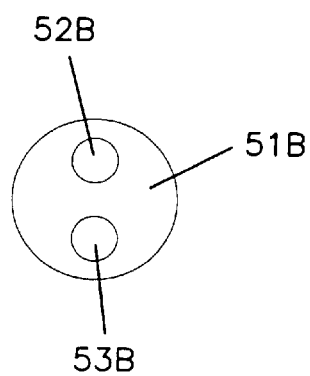
Figure 10C:
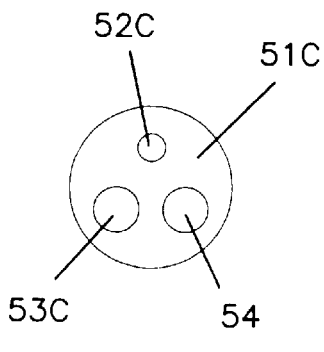

Referring now to FIGS. 10a–10d there are illustrated four cross-sectional views of preferred catheters having at least two lumens. According to the invention, a catheter can include at least one lumen 52a–d for containing an artifact material and a second lumen 53a–d to act as a working channel for tools, suction or injection of liquids. A flexible balk 51a–d separates the lumens. As shown in FIGS. 10a and 10c, the lumens 52(a and c) and 53(a and c) can be a different diameter or both lumens can be the same diameter as in FIG. 10b. Also, as seen in FIG. 10c, in addition to a lumen 52c for containing an artifact material, there may be one or more working lumens, e.g. 53c and 54. Also, the outside shape of the catheter may be any shape suitable for the function of the catheter. Two examples, circular and elliptical, are shown in FIGS. 10a–d.

Figure 10D:
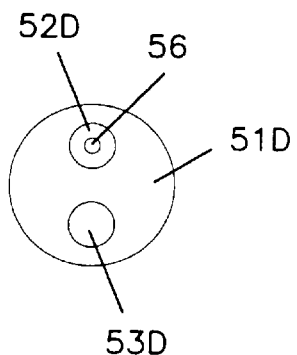

Generally, the lumen for an artifact material is closed at the distal end. FIG. 10d shows a two lumen catheter with a ferromagnetic material, for example, a wire 56, in the lumen for containing an artifact material 52d. Also possible, but not shown in the FIGS. is a one lumen catheter with an artifact material, such as a wire, in the working channel which can be removed.

Figure 11:
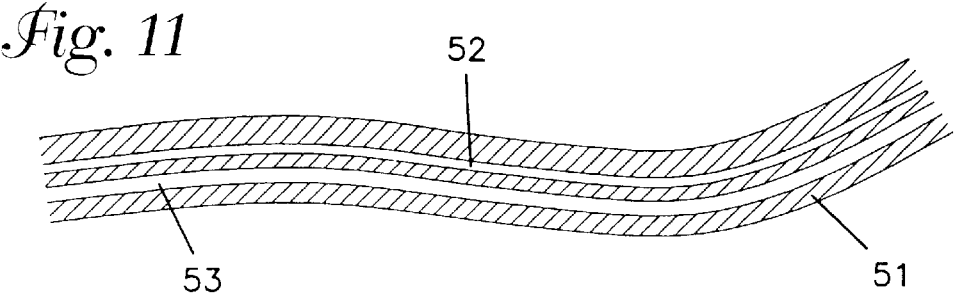
FIG. 11 is a longitudinal cross sectional view of the catheter shown in FIG. 10a taken at A–A'.

FIG. 11 is a longitudinal cross-sectional view of the catheter in FIG. 10a taken at AA'. The use of a liquid artifact material, such as a contrast agent in a lumen, may, for example, produce a positive contrast. In the same way as a contrast liquid, a metallic fiber 56 (FIG. 10d) can be inserted into the lumen in order to control artifact.

Figure 12:
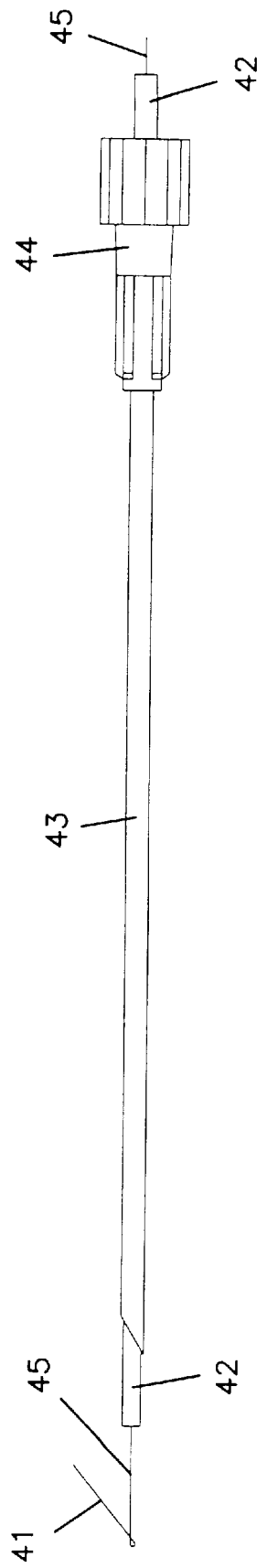
FIG. 12 is a side elevational view of a tumor localizing instrument according to the invention.
Figure 13A:
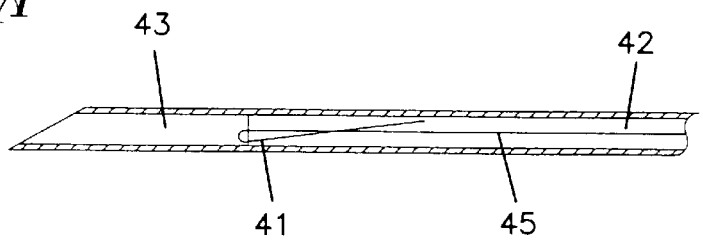
FIGS. 13a–c are longitudinal cross-sectional views of the instrument shown in FIG. 12 in different steps of use.

In another embodiment, shown in FIGS. 12–13a–c, the invention provides a "tumor localizer". According to this embodiment, a localizing wire 45, made out of an artifact material, is inserted into an artifact free tube 42 made from, for example, plastic or ceramic. Both the wire 45 and the artifact free tube 42 are then inserted into a low artifact or artifact free rigid tube 43, which can be connected to a fluid line, syringe, etc., via a connector 44. Preferably, the localizing wire 45 is constructed to include a bend 41 at its distal end to "anchor" into the tissue.

Figure 13B:
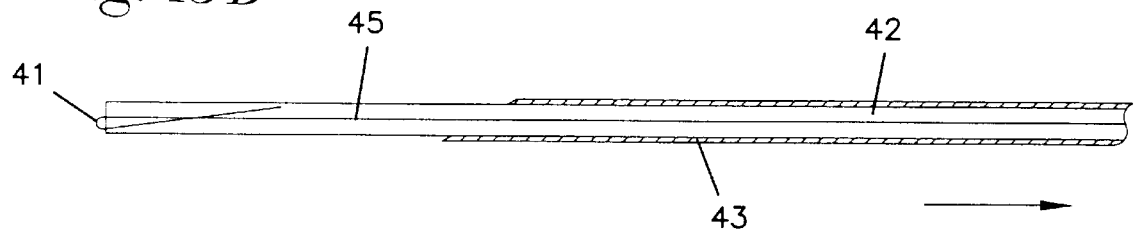
Figure 13C:
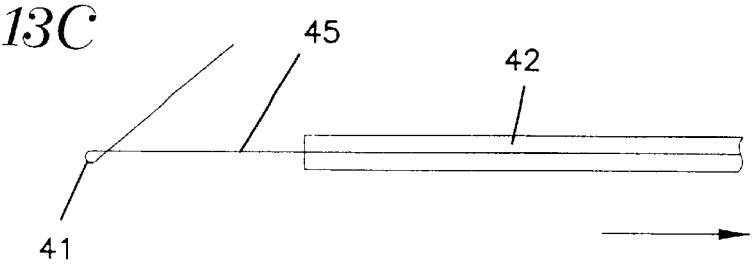

FIGS. 13a–c diagrammatically demonstrates the procedure of use of the tumor localizer. In FIG. 13a, localizing wire 45 and artifact free tube 42 are inserted in outer tube 43. In use, the assembly is pushed through a tissue of the human body until a tumor to be localized is reached without penetrating the tumor. Outer tube 43 is then pulled back and out until only wire 45 and tube 42 remain in the tissue, FIG. 13b. Because wire 45 is an artifact material it shows as an artifact and hence can serve as a guide in the MRI image. Since wire 45 is of low diameter, even an artifact material will give a low level image artifact with low image distortion.

To localize the tumor in front of the "anchor" construction 41, tube 42 is pulled back leaving only the localizer wire 45 in the tissue. Since anchor 41 is constructed as a spring device, it will hold the wire 45 in position. Once wire 45 is in the tumor, the surgeon can use the wire as a guide to localize the tumor for surgical removal.

Suitable "low-artifact" material for outer tube 43 are described in Section I of the specification. Typical material for artifact free tube 42 are any plastic, rubber or ceramic. Examples of plastic includes polypropylene, polyethylene and polyurethane; examples of rubber include silicone. Suitable material for the localizing wire include nickel-chrome-alloy such as ASTM F563-78 comprising 15–25% nickel, 18–22% chromium, up to 4% titanium, up to 4% molybdenum and, up to 6% iron. This material can be purchased from Institute Straumann in 4437 Waldenburg, Switzerland under the trademark SYNTACOBEN. Similar material can be purchased from General Resorts SA in 2501 Bienne, Switzerland under the trademark NIVAFLEX. Preferably, tumor localizer needles are 50 mm to 250 mm long, typically 100 mm to 150 mm. Preferably, the localizing wire is a diameter of 0.1 mm to 0.5 mm, typically 0.2 mm to 0.3 mm. Preferably, the overall diameter of the assembly is 1 mm to 4 mm in diameter, typically 1.5 mm to 2.5 mm.

Plastic instruments are generally not seen in MRI images because they do not contain ferromagnetic compounds. To provide visualization of a plastic material, a metallic material may be evaporated in layers on the plastic.

Typically, however, many plastics are too "soft" of a material to be used for some types of medical instruments. Where increased "hardness" is required, glass fiber reinforced plastic may be used to provide a material suitable for certain medical instruments, for example, cutting instruments. The below described method for enhancing visualization of artifact free materials is suitable for plastic and glass fiber reinforced plastic material. Methods for glass fiber reinforcement are known in the art.

Figure 14:
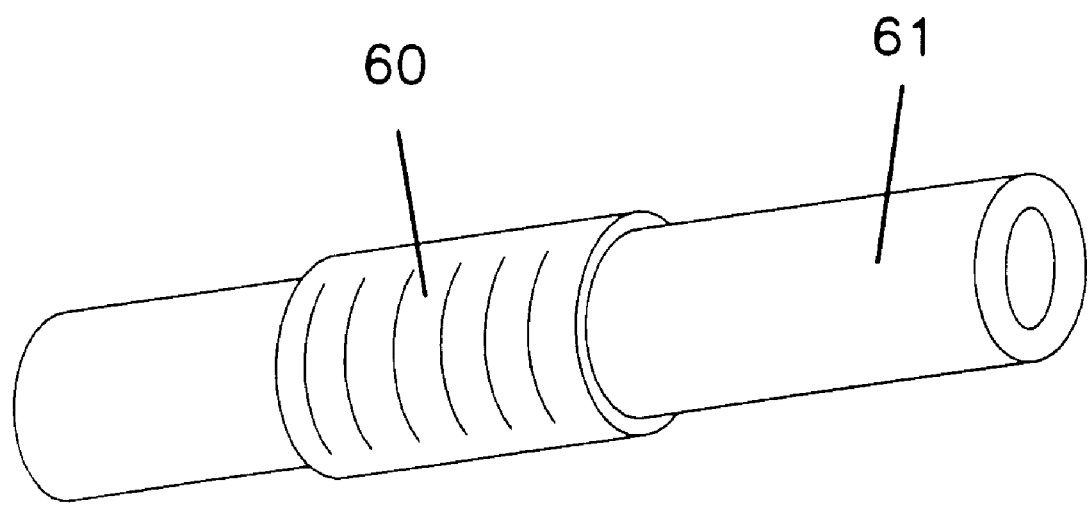
FIG. 14 is a perspective view of a no-artifact material instrument coated with an artifact material.
Figure 15:
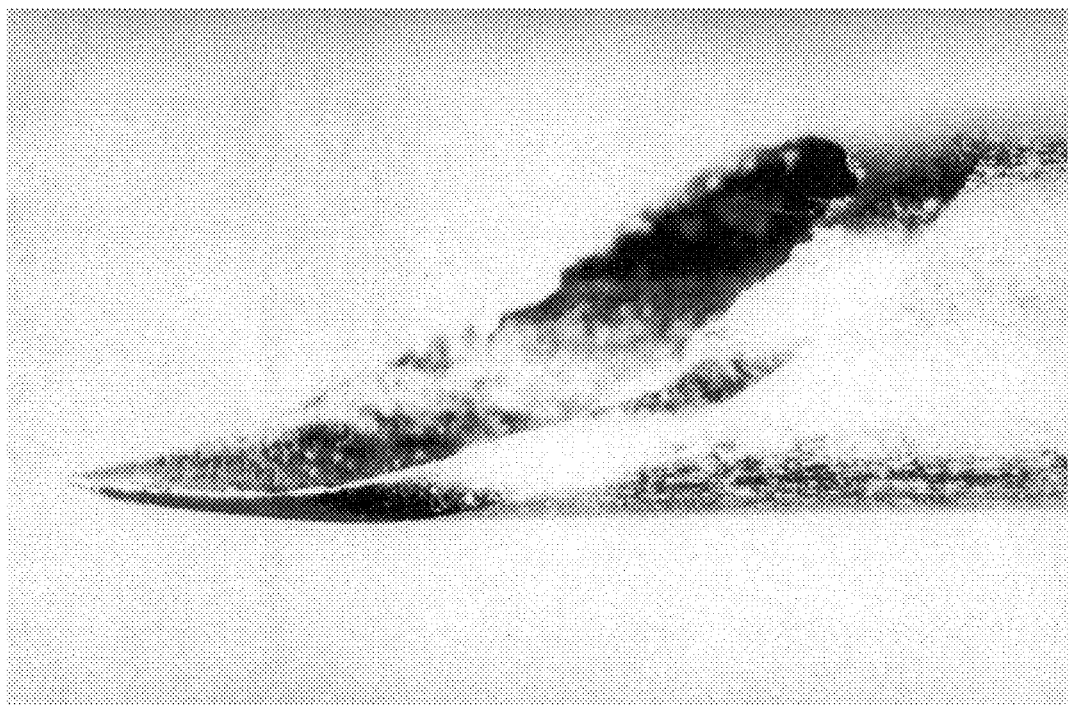
FIG. 15 is a perspective view of a preferred embodiment of a penetrating end of a penetrating instrument of the invention.
Figure 16:
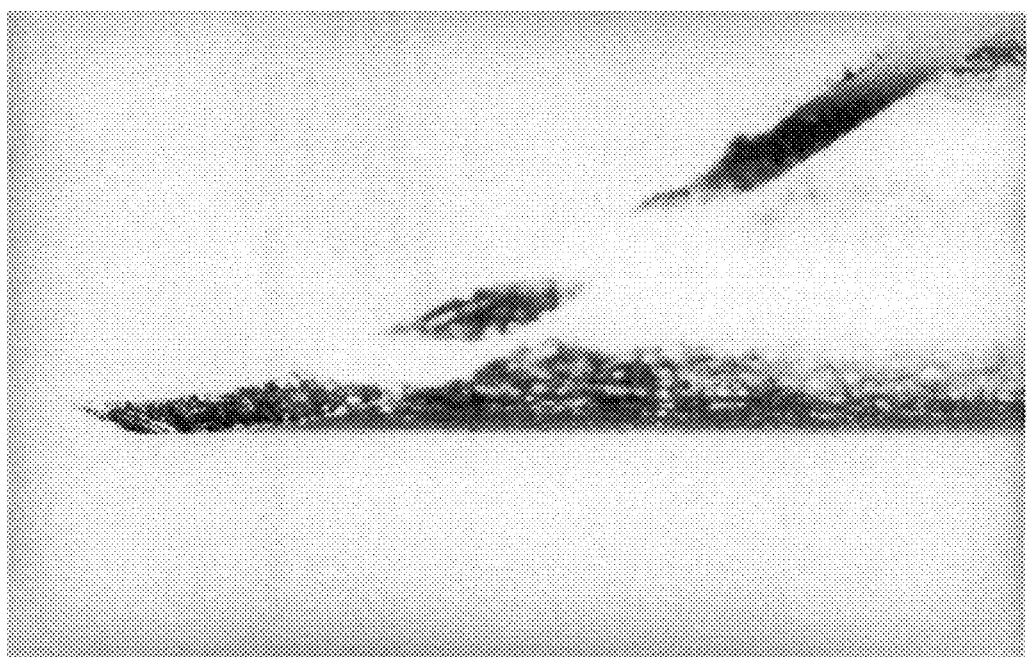
FIG. 16 is a side elevational view of the penetrating end of the embodiment shown in photomicrograph 1.
Figure 17:
FIG. 17 is a front elevational view of the penetrating end of the embodiment shown in FIGS. 15 and 16.
Figure 18:
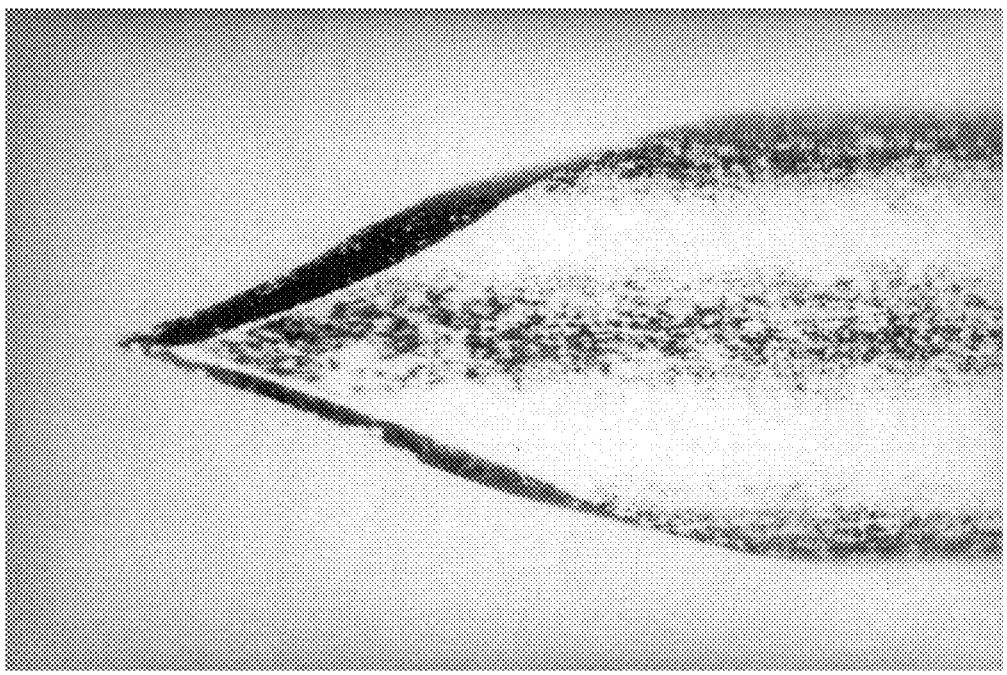
FIG. 18 is a rear elevational view of the penetrating end of the embodiment shown in FIGS. 15–17.

FIG. 14 shows how a plastic tube 61 can be prepared for visualization on an MRI image. Particularly, evaporation, sputtering, plasma deposition, chemical vapor deposition or other thin film depositing method known in the art is used to deposit a thin layer of artifact material onto the plastic tube. The layer 60 can be structured by any thin film structuring technology. Preferably the film thickness is about 2–10 μm.

Alternatively, a thin film, or foil of artifact material can be attached to the plastic tube 61 using standard means (e.g. gluing).

III. IMPROVED PENETRATING END

A titanium alloy instrument of the invention is generally capable of resisting loss of structural configuration when penetrating or cutting a physiological tissue. In another embodiment, however, the present invention is directed to a penetrating instrument, for example, a biopsy needle, epidural needle, injection needle, trocar, etc. with an improved "penetrating end" for enhanced resistance to distortion upon penetration. The penetrating end of the instrument provides an improved cutting edge and distal penetrating tip. The distal tip configuration of the invention also causes less resistance during puncture, thus, reducing structural deformation upon penetration. Such a configuration also, preferably, causes less trauma to the tissue upon insertion.

Referring now to FIG. 1, a "penetrating instrument," 1 of the invention is a hollow tubular structure 2 which is typically elongate with a proximal 3 and distal 4 end.

FIG. 2 is a cross-sectional view taken at (A–A') of FIG. 1 and shows that structure 2 includes a central lumen 5 defined by a cylindrical wall 11 which has an outer 12 and inner (lumenal) 13 surface.

Referring to FIG. 1, both the proximal 3 and distal 4 ends of the instrument 1 open to the exterior providing for passage of a fluid or other flowable material through the lumen 5 of the structure 2.

During use, the proximal end 3 of the penetrating instrument 1 is typically directed towards the operator and may provide a working end, such as a construct 6 for attachment of, for example, a syringe, fluid administration tubing, etc. The "distal end" 4 of the instrument 1 includes the "penetrating end" 7 and typically faces away from the operator when used for tissue penetration. As used herein, the "penetrating end" 7 of the instrument is that end of the instrument which is used to pierce through a membrane, such as a physiological tissue, to provide an opening into the tissue through which the instrument may pass. The distal most aspect of the "penetrating end" is a "penetrating edge". The "penetrating edge" is that aspect of an instrument which actually cuts or pierces the membrane during penetration. Fundamental to the invention, the penetrating edge is formed from the lumenal surface of the cylindrical wall.

Figure 4:
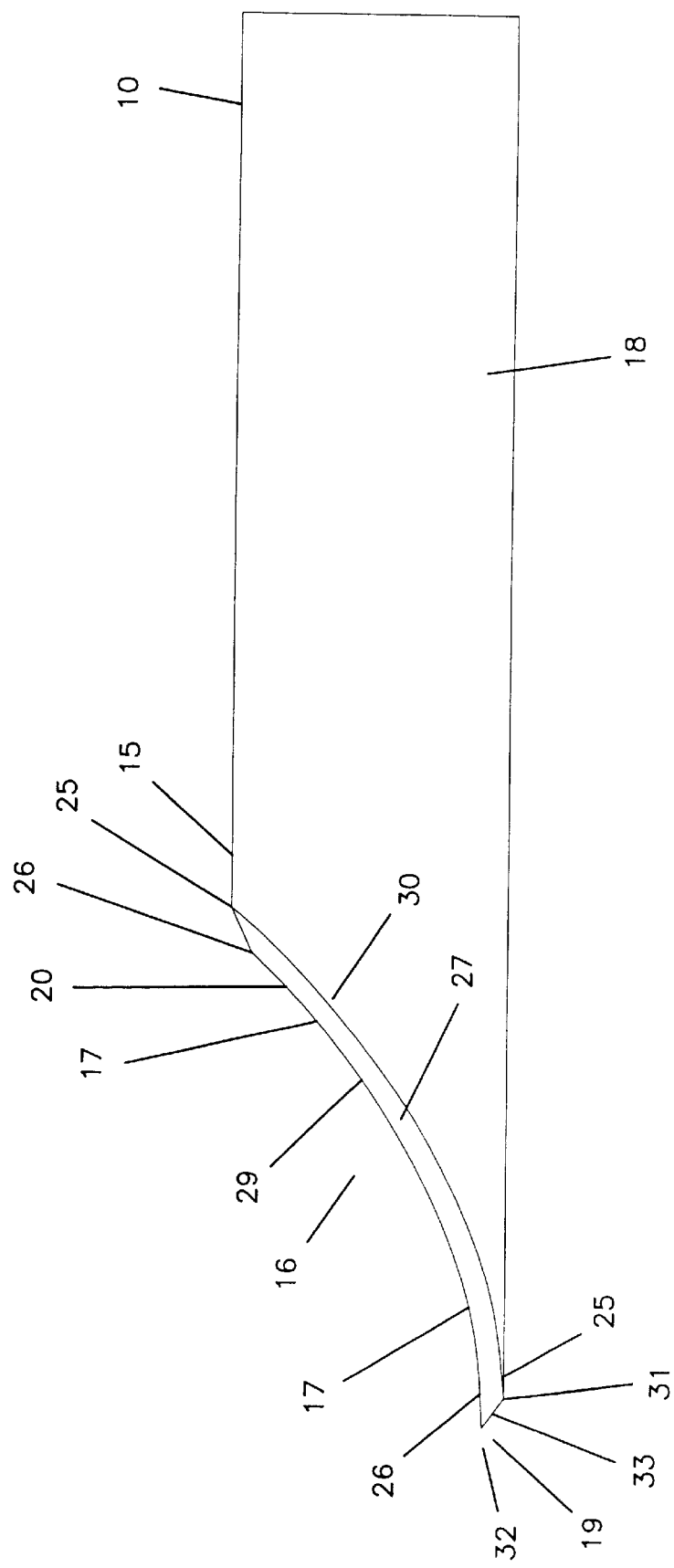
FIG. 4 is a side elevational view of the penetrating end of the instrument shown in FIG. 3.
Figure 5:
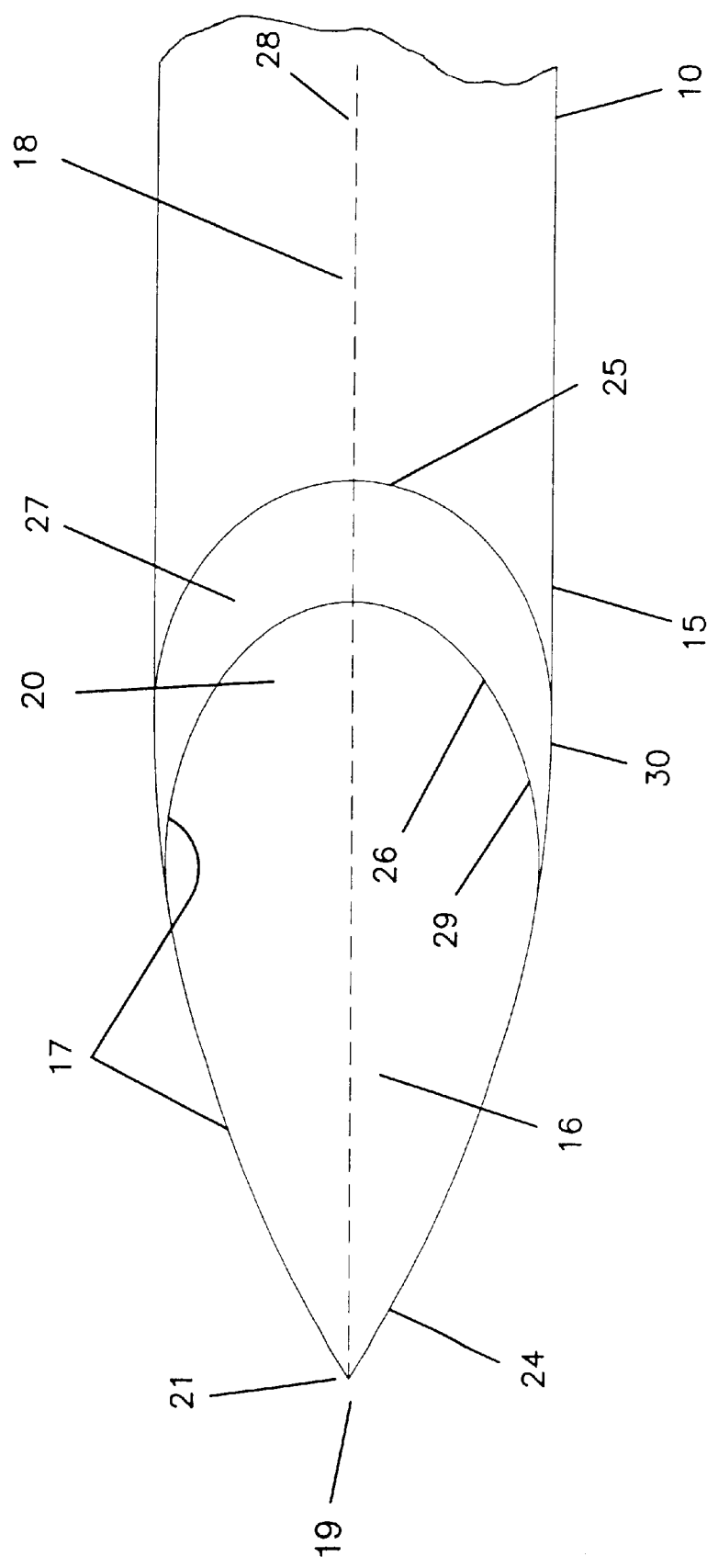
FIG. 5 is a front elevational view of the penetrating end of the instrument shown in FIGS. 3–4.
Figure 6:
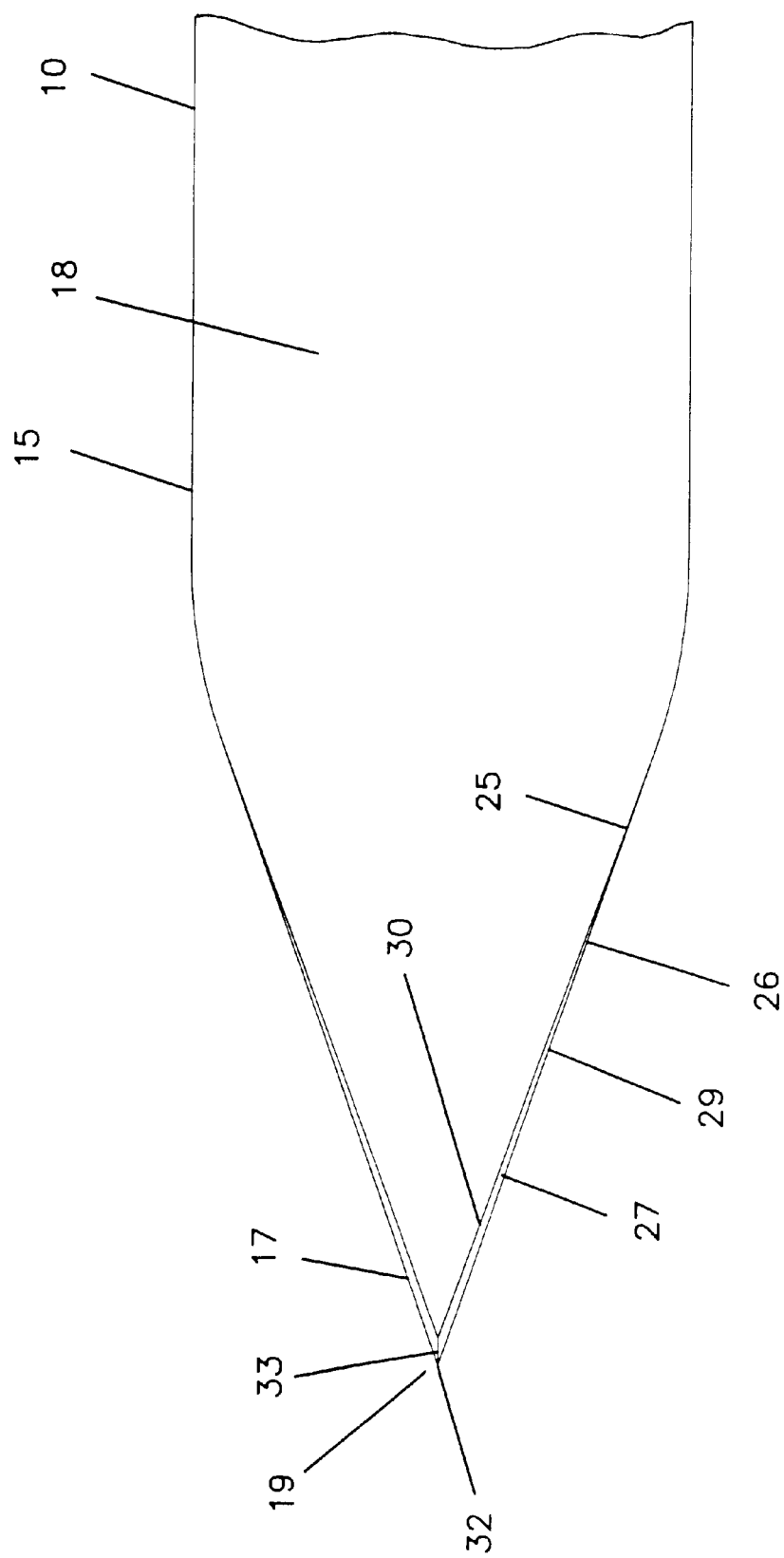
FIGS. 6 is a rear elevational view of the penetrating end of the instrument shown in FIGS. 3–5. The view of the instrument in FIG. 6 is rotated 180° from the view in FIG. 5.

A preferred embodiment of a penetrating end of the invention is further described with reference to FIGS. 3–6. FIG. 3 is a perspective view of an embodiment of a penetrating end 15 of a penetrating instrument 10 of the invention. FIG. 4 is a side elevational view of the penetrating end 15 of the instrument 10 shown in FIG. 3, with the distal lumen opening 16 facing up. FIG. 5 is a front elevational view of the same instrument 10, looking down upon the lumen opening 16 and penetrating edge 17. FIG. 6 is a rear elevational view of the instrument 10, rotated 180 degrees from the view in FIG. 5. Note that the penetrating edge 17 is still visible in this view. The proximal ends of the instruments of FIGS. 3–6 are not shown.

According to the invention, the distal most aspect of the penetrating end 15 is the "penetrating edge" 17. The penetrating edge 17 is the distal most aspect of the cylindrical wall 18 of the instrument 10 which can penetrate a membrane, for example, a physiological tissue, by piercing or cutting. The distal most aspect of the penetrating edge 17 tapers to a distal penetrating tip 19. Referring to FIG. 5, in frontal view, the penetrating edge 17 of the instrument 10 defines a distal lumen opening 16. The distal lumen opening 16 is oval shaped with a proximal base 20 and a distal apex 21 which are oriented the same as the proximal 3 and distal 4 end of the instrument as shown in FIG. 1. Preferably, when looking directly down on the instrument (i.e. perpendicular to horizontal), with the elongate aspect of the instrument horizontal and the distal lumen opening 16 facing "up" (i.e. as in FIG. 5), the penetrating edge 17 bordering the distal lumen opening 16 appears "tear drop" shaped 24. Hence, the penetrating edge 17 tapers distally to the distal apex 21 of the tear drop shape 24 which terminates at the penetrating tip 19. The apex 21 of the tear drop shape 24 provides a "sharper" penetrating tip 19 than, for example, a penetrating tip formed from an elliptical shaped penetrating edge.

Referring now to FIG. 4, when the elongate aspect of the instrument is horizontal, and the distal lumen opening 16 is facing "up", the side view profile of the penetrating edge 17 slopes from the proximal base 20 of the distal lumen opening 16 to the distal apex 21 of the lumen opening 16. In one embodiment, such as that shown, the slope can be parabolic, causing a concave appearance of the penetrating edge 17 in profile. Hence, according to the invention, the taper of the penetrating end 15 may be in at least two dimensions. One taper creating the "tear drop" shape 24 as shown in FIG. 5, and another taper creating the "parabolic" shape shown in the side view of FIG. 4.

Referring to FIGS. 3–6, the components surrounding the penetrating edge 17 will be described further. As see in FIGS. 3–6, the cylindrical wall 18 is beveled from the outer surface of the wall 25 to the inner surface of the wall 26 to create a beveled surface 27 which surrounds the lumen opening 16. As shown in FIG. 5, the beveled surface 27 and the tear drop lumen opening 24 are preferably bilaterally symmetrical relative to axis 28. The beveled surface 27 is contiguous with the penetrating edge 17 and preferably is also "tear drop" shaped. Fundamental to an instrument of the invention is that the beveled surface 27 is beveled such that the penetrating edge 17 of the instrument 10 is the inner (lumenal) 26 surface of the cylindrical wall 18. Hence, the beveled surface 27 has a lumenal aspect 29 which is bounded by, and contiguous with the penetrating edge 17. The beveled surface 27 also has an "anti-lumenal" aspect 30 which is bounded by and contiguous with the outer surface 25 of the cylindrical wall 18.

Referring again to FIGS. 3–6, the distal most aspect of the penetrating end 15 of an instrument 10 of the invention is the "penetrating tip" 19. Preferably, as shown in FIGS. 3–4 the penetrating tip 19 of the invention has a "beak" configuration 31. As used herein, a preferred "beak" 31 configuration has a "penetrating point" 32 defined by the intersection of three surfaces. The three surfaces defining the penetrating point 32 are: the distal most aspect of the inner surface 26 of the cylindrical wall 18 and the distal most aspect of the lumenal aspect 29 of the bilaterally symmetrical beveled surface 27.

Preferably, the intersection of the distal most aspect of the bilaterally symmetrical beveled surfaces 27, also form a "distal tip penetrating edge" 33. The distal tip penetrating edge also intersects with the inner surface 26 and outer surface 25 of the cylinder wall 18 at its most distal extent.

In a particularly preferred embodiment, a "beak" configuration is as shown in FIGS. 15–18, which illustrate the embodiment illustrated in FIGS. 3–6 respectively. FIGS. 15–18 are provided to fully define a particularly preferred embodiment of a penetrating end of the invention. The photomicrographs may provide enhancement of the textual recitation of the cooperative relationship of the elements of a preferred penetrating tip 19 of the invention.

Figure 7:
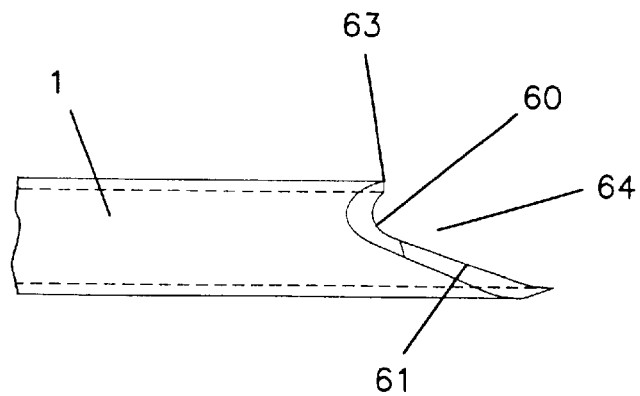
FIG. 7 is a side elevational view of another embodiment of the penetrating end of a penetrating instrument of the invention.
Figure 8:
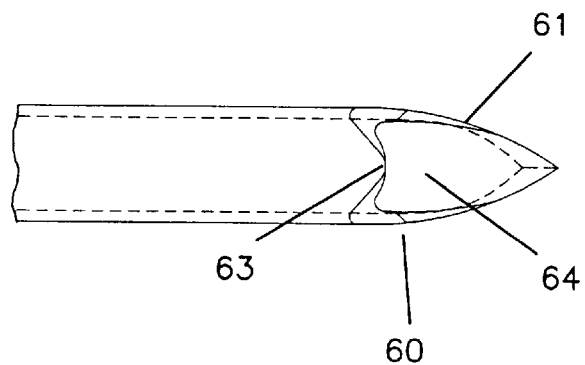
FIG. 8 is a front elevational view of the same instrument shown in FIG. 7.
Figure 9:
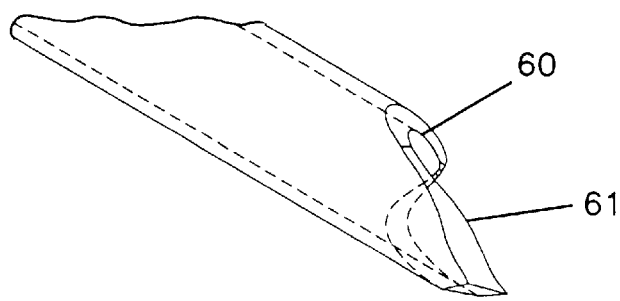
FIG. 9 is a perspective view of the same instrument shown in FIGS. 7–8.

FIGS. 7–9 show another embodiment of a penetrating instrument of the invention. According to this embodiment, a bilateral facet 60, is created in the penetrating edge 61 near the proximal aspect 63 of the lumen opening 64. The facet may provide increased stability of the distal penetrating tip.

Referring to FIGS. 3–6, in typical use, the penetrating point 32, followed by the distal tip penetrating edge 33 are the areas of the penetrating end which first pierce a physiological tissue upon penetration.

According to the invention, a penetrating instrument may be about 50 mm to 200 mm, preferably 100 mm to 150 mm long. The inside diameter of an instrument, for example, a needle, may be about 0.2 mm to 10.0 mm, preferably about 0.5 mm to 2.0 mm. The outside diameter of a needle of the invention may be about 0.4 mm to 11.0 mm, preferably, about 0.7 mm to 2.2 mm. A preferred cylindrical wall thickness for a needle of the invention is about 0.09 mm to 0.11 mm.

The distal tip of a penetrating instrument of the invention can also be coated with, for example, a hard alloy such as titanium nitrite, which may further reduce the possibility for configurational deformation upon penetration as well as providing increased cutting ability.

The above specification and data provide a complete description of the preparation of the medical instruments and methods of the invention. Since many embodiments of the invention can be made without departing from the spirit and scope of the invention, the invention resides in the claims hereinafter appended.

What is claimed:

1. A method for removing magnetic contaminants from the surface of an alloy material, the method comprising a step of:
   (a) preparing a wet chemical etching composition comprising:
      (i) an acid, HX, wherein X is a halogen; and
      (ii) nitric acid; and
   (b) contacting the alloy material with the wet chemical etching composition.

2. The method according to claim 1 wherein the halogen is fluorine.

3. The method according to claim 2, wherein the wet chemical etching composition includes hydrofluoric acid.

4. The method according to claim 2 wherein the wet chemical etching composition is prepared from 40% hydrofluoric acid and 65% nitric acid.

5. The method according to claim 1 wherein the halogen is chlorine.

6. The method according to claim 5, wherein the wet chemical etching composition includes hydrochloric acid.

7. The method according to claim 5 wherein the wet chemical etching composition is prepared from 25% hydrochloric acid and 25% nitric acid.

8. The method according to claim 1 wherein the alloy material is a titanium alloy.

9. The method according to claim 8 wherein the alloy material is in a medical instrument.

10. The method according to claim 9 wherein the medical instrument is a needle.

11. A medical instrument comprising:
   an elongated member having a penetrating distal end, the member having a metal surface substantially free of magnetic contaminants prepared using a method of removing magnetic contaminants comprising,
      (a) preparing a wet chemical etching composition comprising:
         (i) an acid, HX, wherein X is a halogen; and
         (ii) nitric acid; and
      (b) contacting the medical instrument with the wet chemical etching composition.

12. The instrument according to claim 11 wherein the halogen is fluorine.

13. The instrument according to claim 12 wherein the wet chemical etching composition is prepared from 40% hydrofluoric acid and 65% nitric acid.

14. The instrument according to claim 11 wherein the halogen is chlorine.

15. The instrument according to claim 14 wherein the wet chemical etching composition is prepared from 25% hydrochloric acid and 25% nitric acid.

16. The instrument according to claim 11 wherein the metal surface is formed, at least in part, from a titanium alloy.

17. The instrument according to claim 11 wherein the medical instrument is a needle.

18. The instrument according to claim 11, wherein the method of removing magnetic contaminants further comprises applying a surface lubricant to the medical instrument after contacting the medical instrument with the wet chemical etching composition.

19. The instrument according to claim 18 wherein the surface lubricant comprises silicon.

20. The instrument according to claim 19 wherein the silicon is present in the surface lubricant at a concentration of about 5–20%.

* * * * *